United States Patent
Leonard et al.

(10) Patent No.: US 6,549,797 B1
(45) Date of Patent: Apr. 15, 2003

(54) ELECTRODE REMOVER FOR A PERCUTANEOUS ELECTRICAL THERAPY SYSTEM

(75) Inventors: Paul Leonard, Woodinville, WA (US); Jon M. Bishay, Woodinville, WA (US)

(73) Assignee: Vertis Neuroscience, Inc., Seattle, WA (US)

(*) Notice: Subject to any disclaimer, the term of this patent is extended or adjusted under 35 U.S.C. 154(b) by 0 days.

(21) Appl. No.: 09/451,796

(22) Filed: Dec. 1, 1999

(51) Int. Cl.$^7$ ............................. A61N 1/02; A61N 1/04

(52) U.S. Cl. ........................ 600/372; 607/115; 128/907

(58) Field of Search .................................. 600/386, 372, 600/382, 548; 607/115, 145, 148, 149; 128/907, DIG. 26

(56) References Cited

U.S. PATENT DOCUMENTS

| | | | |
|---|---|---|---|
| 3,030,959 A | 4/1962 | Grunert | 606/182 |
| 3,090,151 A | 5/1963 | Stewart et al. | 43/6 |
| 3,208,452 A | 9/1965 | Stern | 606/182 |
| 3,938,526 A | 2/1976 | Anderson et al. | 606/189 |
| 3,943,935 A | 3/1976 | Cameron | 606/188 |
| 3,983,881 A | 10/1976 | Wickham | 607/43 |
| 4,139,011 A * | 2/1979 | Benoit et al. | 128/329 R |
| 4,153,059 A | 5/1979 | Fravel et al. | 607/41 |
| 4,207,903 A | 6/1980 | O'Neill | 607/131 |
| 4,256,116 A | 3/1981 | Meretsky et al. | 607/46 |
| 4,262,672 A | 4/1981 | Kief | |
| 4,281,659 A * | 8/1981 | Farrar et al. | 600/351 |

(List continued on next page.)

FOREIGN PATENT DOCUMENTS

| | | | |
|---|---|---|---|
| FR | 2500745 | 9/1982 | A61N/1/36 |

OTHER PUBLICATIONS

AAMI Neurosurgery Committee; AAMI Implantable Neurostimulator Subcommittee. Implantable peripheral nerve stimulators. Assoc. for the Advancement of Medical Instrumentation (1995) NS15–1995, cover–8, 11 pages.**

Almay, B.G.L. et al., "Long–Term High–Frequency Transcutaneous Electrical Nerve Stimulation (hi–TNS) in Chronic Pain. Clinical Response and Effects of CSF–Endorphins, Monoamine Metabolites, Substance P–Like Immunoreactivity (SPLI) and Pain Measures", J. Physchosom.Res. (1985) 29:247–257, 11 pages.

Baker, L. et al., "Effects of Waveform on Comfort During Neuromuscular Electrical Stimulation", Clinical Orthopedics and Related Research (Aug. 1988) 233:75–85.

Balogun, J., "Effects of Ramp Time on Sensory, Motor and Tolerance Thresholds During Exogenous Electrical Stimulation", The Journal of Sports Medicine and Physical Fitness (Dec. 1991) 3:4, 521–526.

BD Safety Products. BD Vacutainer Safety–Lok Blood Collection Set; BD Vacutainer SafetyGlide Blood Collection Assembly and BD Vacutainer Eclipse Blood Collection Needle, 1 page.

BD Safety Flow Lancet—Product No. 366356. BD catalog 1997–2000, Capillary Access, http://catalog.bd.com/scripts/OBDsheet.exe?FNC=productlist_Alistproducts_html_366356 (Aug. 7, 2001) (3 pages).

BD Vacutainer SafetyGlide Blood Collection Assembly. Quick Reference Card (1999), 1 page.

(List continued on next page.)

*Primary Examiner*—Carl Layno
(74) *Attorney, Agent, or Firm*—Perkins Coie LLP

(57) ABSTRACT

In a preferred embodiment, a percutaneous electrode remover includes a housing adapted to be held in a user's hand, the housing having an aperture at a distal end; and an actuator operable by a user to move a precutaneously inserted electrode through the aperture and completely into the housing.

4 Claims, 3 Drawing Sheets

U.S. PATENT DOCUMENTS

| | | | |
|---|---|---|---|
| 4,284,856 A | 8/1981 | Hochmair et al. | 607/9 |
| 4,381,012 A | 4/1983 | Russek | 600/382 |
| 4,408,617 A | 10/1983 | Auguste | 600/548 |
| 4,431,000 A | 2/1984 | Butler et al. | 607/73 |
| 4,437,467 A * | 3/1984 | Helfer et al. | 600/376 |
| 4,541,432 A | 9/1985 | Molina-Negro et al. | 607/46 |
| 4,556,064 A | 12/1985 | Pomeranz et al. | 607/66 |
| 4,685,466 A | 8/1987 | Rau | 600/387 |
| 4,686,996 A * | 8/1987 | Ulbrich | 600/376 |
| 4,712,558 A | 12/1987 | Kidd et al. | 607/48 |
| D297,047 S | 8/1988 | Hon et al. | D24/187 |
| 4,765,310 A | 8/1988 | Deagle et al. | |
| 4,895,154 A | 1/1990 | Bartelt et al. | 607/50 |
| 4,934,371 A * | 6/1990 | Malis et al. | 600/377 |
| 4,949,734 A * | 8/1990 | Bernstein | 128/897 |
| 4,979,508 A | 12/1990 | Beck | 607/54 |
| 5,012,811 A | 5/1991 | Malis et al. | 600/376 |
| D318,330 S | 7/1991 | Doty et al. | D24/187 |
| 5,036,850 A | 8/1991 | Owens | 607/66 |
| 5,054,486 A | 10/1991 | Yamada | 607/3 |
| 5,094,242 A | 3/1992 | Gleason et al. | |
| 5,117,826 A | 6/1992 | Bartelt et al. | 607/46 |
| 5,211,175 A | 5/1993 | Gleason et al. | |
| 5,246,014 A | 9/1993 | Williams et al. | 607/122 |
| 5,281,218 A | 1/1994 | Imran | 606/41 |
| 5,332,401 A | 7/1994 | Davey et al. | |
| D357,069 S | 4/1995 | Plahn et al. | D24/187 |
| 5,439,440 A | 8/1995 | Hofmann | 604/20 |
| 5,449,378 A | 9/1995 | Schouenborg | |
| 5,593,429 A | 1/1997 | Ruff | 607/116 |
| 5,649,936 A | 7/1997 | Real | 606/130 |
| 5,682,233 A | 10/1997 | Brinda | 356/246 |
| 5,702,359 A | 12/1997 | Hofmann et al. | 604/20 |
| 5,810,762 A | 9/1998 | Hofmann | 604/20 |
| 5,851,223 A | 12/1998 | Liss et al. | 607/46 |
| 5,861,015 A | 1/1999 | Benja-Athon | |
| 5,873,849 A | 2/1999 | Bernard | 604/20 |
| 5,928,144 A * | 7/1999 | Real | 600/378 |
| 5,941,845 A | 8/1999 | Tu et al. | 604/53 |
| 5,968,011 A | 10/1999 | Larsen et al. | 604/288.02 |
| 5,968,063 A * | 10/1999 | Chu et al. | 606/185 |
| 6,009,347 A | 12/1999 | Hofmann | 604/21 |
| 6,035,236 A | 3/2000 | Jarding et al. | 607/53 |
| 6,050,992 A | 4/2000 | Nichols | 606/41 |
| 6,068,650 A | 5/2000 | Hofmann et al. | 607/2 |
| 6,117,077 A | 9/2000 | Del Mar et al. | 600/301 |
| 6,122,547 A | 9/2000 | Benja-Athon | 607/46 |
| 6,208,893 B1 | 3/2001 | Hofmann | 604/21 |
| 6,269,270 B1 | 7/2001 | Boveja | 607/45 |
| 6,355,021 B1 | 3/2002 | Nielsen et al. | 604/263 |

OTHER PUBLICATIONS

Brull, S., Silverman, D.G., "Pulse Width, Stimulus Intensity, Electrode Placement, and Polarity During Assessment of Neuromuscular Block", Anesthesiology (Oct. 1995) 83:702–709.

Carroll, D., "Randomization is Important in Studies with Pain Outcomes: Systematic Review of Transcutaneous Electrical Nerve Stimulation in Acute Postoperative Pain", Br J Anaesth. (1996) 77:798–803**.

Cassuto, J. et al., "The Use of Modulated Energy Carried on a High Frequency Wave for the Relief of Intractable Pain", Int.J.Clin.Pharm.Res. (1993) XIII(4) 239–241**.

Cramp AF et al., "The Effect of High and Low Frequency Transcutaneous Electrical Nerve Stimulation Upon Cutaneous Blood Flow and Skin Temperature in Healthy Subjects", Clin.Physio. (2000) 20:150–7.

Eclipse+ Dual Channel Transcutaneous Electrical Nerve Stimulator User's Manual (1993), 31 pages**.

Electrotherapy for Rehabilitation, Empi Cervical Traction, http://www.empi.com/b/b2.htm, Oct. 22, 2001, 3 pages.

EPIX XL TENS Instruction Manual, Empi, Inc. (1988), 21 pages**.

Foster, N. et al., Manipulation of Transcutaneous Electrical Nerve Stimulation Variables Has No Effect on Two Models of Experimental Pain in Humans, The Clinical Journal of Pain (1996) 12:301–310**.

Galletti S.P. et al., Highlights concerning low frequency–high intensity TENS (review). Minerva Stomatol (1995) 44:421–9**.

Ghoname et al., "Does the Stimulus Frequency Affect the Analgesic Response to Electrical Stimulation?", Anesth. Analg. (1999) 88:S210, 1 page.

Gopalkrishnann, P., Sluka, K.A., "Effect of Varying Frequency, Intensity, and Pulse Duration of Transcutaneous Electrical Nerve Stimulation on Primary Hyperalgesia in Inflamed Rats", Arch.,Phys.Med.Rehabil. (Jul. 2000) 81:984–990.

Gracanin, F., Trnkoczy, A. "Optimal Stimulus Parameters for Minimum Pain in the Chronic Stimulation of Innervated Muscle", Arch.Phys.Med. Rehabil. (Jun. 1975) 56:243–249.

Hamza, M.A. et al., "Effect of the Duration of Electrical Stimulation on the Analgesic Response in Patients with Low Back Pain", Anesthesiology (Dec. 1999), V. 91, No. 6:1622–7.

Hamza MA et al., "Effect of the frequency of transcutaneous electrical nerve stimulation on the postoperative opioid analgesic requirement and recovery profile", Anesthesiology (Nov. 1999) 91:1232–8.

Han JS et al., "Effect of Low and High–Frequency TENS on Met–enkephalin–Arg–Phe and Dynorphin A Immunoreactivity in Human Lumbar CSF", Pain (1991) 47:295–8**.

Healthronics HANS LY257 User Manual, 15 pages.

Innovative Healthcare: Electrotherapy Pain & Rehabilitation Product Solutions from Rehabilicare. [Includes product description of SporTX and Ortho DX]. 1999, 3 pages, http://www.mvpdesign.com/sites/rehavilicare/all_products.html.

Instruction Manual for the Empi EPIX VT TENS Device, 1997, Dual Channel Transcutaneous Electrical Nerve Stimulator, Empi, Inc., 29 pages**.

Intelect Legend Stim Clinical Reference Manual, vol. 4 Intelect Legend Series, Chattanooga Group, Inc., 31 pages.

Jette, D., "Effect of Different Forms of Transcutaneous Electrical Nerve Stimulation on Experimental Pain", Physical Therapy (Feb. 1986) 66:2, 187–193.

Johnson, M.I., "Analgesic Effects of Different Pulse Patterns of Trancutaneous Electrical Nerve Stimulation on Cold–induced Pain in Normal Subjects", Journal of Psychosomatic Research (1991) 35:2–3; 313–321**.

Johnson, MI, "Analgesic Effects of Different Frequencies of Transcutaneous Electrical Nerve Stimulation on Cold–Induced Pain in Normal Subjects", Pain (1989) 39:231–6**.

Johnson, MI, et al. "An In–Depth Study of Long–Term Users of Transcutaneous Electrical Nerve Stimulation (TENS). Implications for Clinical Use of TENS", Pain (1991) 44:221–9**.

Katims, J.J. et al., "Transcutaneous Nerve Stimulation. Frequency and Waveform Specificity in Humans", Appl. Neurophysiol (1986) 49:86–91**.

Leem, J., "Electrophysiological evidence for the antinociceptive effect of transcutaneous electrical stimulation on mechanically evoked responsiveness of dorsal horn neurons in neuropathic rats", Neuroscience Letters (1995) 192:197–200**.

Liss S., Liss B., "Physiological and Therapeutic Effects of High Frequency Electrical Pulses", Integr.Physio.Behav. Sci. (Apr.–Jun. 1996) 31:88–94.

Model AWQ–104B Multi–Purpose Electronic Acupunctoscope Instruction Manual, 10 pages.

Marchand, S., et al., "Modulation of Heat Pain Perception by High Frequency Transcutaneous Electrical Nerve Stimulation (TENS)", Clin.J.Pain. (1991) 7:122–9**.

Moreno–Aranda J., "Electrical Parameters for over–the–skin muscle stimulation", J. Biomechanics (1981) 14:9, 579–585**.

Moreno–Aranda J., Seireg, A., "Investigation of over–the–skin electrical stimulation parameters for different normal muscles and subjects", J. Biomechanics (1981) 14:9: 587–593**.

O'Brien, WJ, "Effect of Transcutaneous Electrical Nerve Stimulation on Human Blood B–Endorphin Levels", Physical Therapy (Sep. 1984) 64:1367–1374.

Ordog, G., "Transcutaneous Electrical Nerve Stimulation Versus Oral Analgesic: A Randomized Double–Blind Controlled Study in Acute Traumatic Pain", American Journal of Emergency Medicine (Jan. 1987) 5:1, 6–10.

Ortho DX Product Data Sheet.

Pointer F–3 Instruction Manual, ITO Co., Ltd., 10 pages.

Rooney, J.G., et al., "Effect of Variation in the Burst and Carrier Frequency Modes of Neuromusclar Electrical Stimulation on Pain Perception of Healthy Subjects", Phys. Ther. (Nov. 1992) 72:11, 800–808.

Sluka, K.A., "Treatment with Either High or Low Frequency TENS Reduces the Secondary Hyperalgesia Observed After Injection of Kaolin and Carrageenan into the Knee Joint", Pain (1998) 77:97–102.

SMP–plus. The Pain Relief Solution for Hard to Treat Patients, Rehabilicare (2 pages).

Somers, D.L., "High–Frequency Transcutaneous Electrical Nerve Stimulation Alters Thermal but not Mechanical Allodynia Following Chronic Constriction Injury of the Rat Sciatic Nerve", Arch.Phys.Med.Rehabil. (Nov. 1998) 79:1370–6.

SPORTX Product Data Sheet.

Starobinets, M., Volkova, L., [Analgesic Effect of High–Frequency and Acupuncture–Like Trancutaneous Electric Stimulation of Nerve Fibers in Spinal Osteochondritis]. Zh Nevropatol Psikhiatr Im S. S. Korsakova (1985) 85:350–4**.

Van Doren, CL, "Contours of Equal Percieved Amplitude and Equal Percieved Frequency for Electrocutaneous Stimuli", Percept. Phychophys. (1997) 59:613–22**.

White, P.F., et al. "Percutaneous Neuromodulation Therapy: Does the Location of Electrical Stimulation Effect the Acute Analgesic Response?", Anesth. Analg. (2000) 91:1–6.

White, P.F. et al., "The Effect of Montage on the Analgesic Response to Percutaneous Neuromodulation Therapy", Anesth. Analg. (2001) 92:483–7.

U.S. patent application No. 09/452,477, entitled "Percutaneous Electrical Therapy System with Electrode Entry Angle Control," filed on Dec. 1, 1999, Attorney Docket No. 337348004US.

U.S. patent application No. 09/452,663, entitled "Percutaneous Electrical Therapy System Providing Electrode Axial Support," filed on Dec. 1, 1999, Attorney Docket No. 337348005US.

U.S. patent application No. 09/452,508, entitled "Percutaneous Electrical Therapy System with Electrode Depth Control," filed on Dec. 1, 1999, Attorney Docket No. 337348006US.

U.S. patent application No. 09/451,795, entitled "Percutaneous Electrical Therapy System with Position Maintenance," filed on Dec. 1, 1999, Attorney Docket No. 337348007US.

U.S. patent application No. 09/451,799, entitled "Electrode Introducer for a Percutaneous Electrical Therapy System," filed on Dec. 1, 1999, Attorney Docket No. 337348008US.

U.S. patent application No. 09/452,510, entitled "Percutaneous Electrical Therapy System for Minimizing Electrode Insertion Discomfort," filed on Dec. 1, 1999, Attorney Docket No. 337348009US.

U.S. patent application No. 09/451,800, entitled "Electrode Assembly for a Percutaneous Electrical Therapy System," filed on Dec. 1, 1999, Attorney Docket No. 337348010US.

U.S. patent application Ser. No. 09/451,547, entitled "Percutaneous Electrical Therapy System with Sharp Point Protection," filed on Dec. 1, 1999, Attorney Docket No. 337348012US.

Ahmed et al., "Percutaneous Electrical Nerve Stimulation (PENS): A Complementary Therapy for the Management of Pain Secondary to Bony Metastasis," Clinical Journal of Pain 14:320–3 (1998).

Ahmed et al., "Percutaneous Electrical Nerve Stimulation: An Alternative to Antiviral Drugs for Herpes Zoster," Anesth. Analg. 87:911–4 (1998).

Ballegaard et al., "Acupuncture and Transcutaneous Electric Nerve Stimulation in the Treatment of Pain Associated with Chronic Pancreatitis," Scan.J.Rehab.Med. 20:1249–54 (1985).

Balogun et al., "The effects of acupuncture, electroneedling and transcutaneous electrical stimulation therapies on peripheral haemodynamic functioning," Disability and Rehab. 20:41–8 (1998).

Bushnell et al., "Electrical stimulation of peripheral and central pathways for the relief of musculoskeletal pain," Can.J.Physiol.Pharmacol. 69:697–703 (1991).

Cheng et al., "Electrotherapy of Chronic Musculoskeletal Pain: Comparison of Electroacupuncture and Acupuncture–Like Transcutaneous Electrical Nerve Stimulation," Clin.J-.Pain 2:143–9 (1987).

Cheng et al., "Electroacupuncture analgesia could be mediated by at least two pain–relieving mechanisms: endorphin and non–endorphin systems," Life Sciences 25:1957–62 (1979).

Cheng et al., "Electroacupuncture elevates blood cortisol levels in naive horses; sham treatment has no effect," Intern.J.Neuroscience 10:95–7 (1980).

Gadsby et al., "Nerve stimulation for low back pain—a review," Nursing Standard 11:32–3 (1997).

Ghoname et al., "Percutaneous electrical nerve stimulation: an alternative to TENS in the management of sciatica," Pain 83:193–9 (1999).

Ghoname et al., "Percutaneous Electrical Nerve Stimulation for Low Back Pain," JAMA 281:818–23 (1999).

Ghoname et al., "The Effect of Stimulus Frequency on the Analgesic Response to Percutaneous Electrical Nerve Stimulation in Patients with Chronic Low Back Pain," Anesth.Analg. 88:841–6 (1999).

Ghoname et al., "The effect of the duration of electrical stimulation on the analgesic response," Anesth.Analg. 88:S211 (1999).

Landau et al., "Neuromodulation Techniques for Medically Refractory Chronic Pain," Annu.Rev.Med. 44:279–87 (1993).

Lehmann et al., "Efficacy of Electroacupuncture and TENS in the Rehabilitation of Chronic Low Back Pain Patients," Pain 26:277–90 (1986).

Omura, "Basic electrical parameters for safe and effective electro–therapeutics [electroacupuncture, TES, TENMS (or TEMS), TENS and electro–magnetic field stimulation with or without drug field] for pain, neuromuscular skeletal problems, and circulatory disturbances," Acupuncture & Electro–Therapeutics Res. 12:201–25 (1987).

Omura, "Electrical parameters for safe and effective electro–acupuncture and transcutaneous electrical stimulation: Threshold potentials for tingling, muscle contraction and pain; and how to prevent adverse effects of electro–therapy," Acupuncture & Electro–Therapeutics Res. 10:335–7 (1985).

Romita et al., "Parametric Studies on Electroacupuncture–Like Stimulation in a Rat Model: Effects of Intensity, Frequency, and Duration of Stimulation on Evoked Antinociception," Brain Res.Bull. 42:289–96 (1997).

Ulett et al., "Electroacupuncture: Mechanisms and Clinical Application," Biol.Psych. 44:129–38 (1998).

Radioionics RFG–3C product brochure (1997).

Rehabilicare Ortho Dx product brochure.

Rehabilicare SporTX product brochure.

* cited by examiner

ELECTRODE REMOVER FOR A PERCUTANEOUS ELECTRICAL THERAPY SYSTEM

BACKGROUND OF THE INVENTION

This invention relates generally to percutaneous electrical therapy systems for medical use. In particular, the invention relates to an electrode remover for removing percutaneously inserted electrodes from a patient's tissue.

Electrical therapy has long been used in medicine to treat pain and other conditions. For example, transcutaneous electrical nerve stimulation (TENS) systems deliver electrical energy through electrode patches placed on the surface of a patient's skin to treat pain in tissue beneath and around the location of the patches. The efficacy of TENS systems in alleviating pain is questionable at best, however.

More recently, a technique in which electrodes are placed through the patient's skin into the target tissue has been proposed. Percutaneous Neuromodulation Therapy ("PNT") (also sometimes called Percutaneous Electrical Nerve Stimulation or "PENS") using percutaneously placed electrodes achieves significantly better pain relief results than TENS treatments using skin surface electrodes. This therapy is described in Ghoname et al., "Percutaneous Electrical Nerve Stimulation for Low Back Pain," JAMA 281:818–23 (1999); Ghoname et al, "The Effect of Stimulus Frequency on the Analgesic Response to Percutaneous Electrical Nerve Stimulation in Patients with Chronic Low Back Pain," Anesth. Analg. 88:841–6 (1999); Ahmed et al., "Percutaneous Electrical Nerve Stimulation (PENS): A Complementary Therapy for the Management of Pain Secondary to Bony Metastasis," Clinical Journal of Pain 14:320–3 (1998); and Ahmed et al., "Percutaneous Electrical Nerve Stimulation: An Alternative to Antiviral Drugs for Herpes Zoster," Anesth. Analg. 87:911–4 (1998). The contents of these references are incorporated herein by reference.

Thus far, PNT practitioners have used percutaneously placed acupuncture needles attached to waveform generators via cables and alligator clips to deliver the therapy to the patient. This arrangement and design of electrodes and generator is far from optimal. For example, removal of percutaneous electrodes has thus far been a cumbersome operation. It has also been dangerous, since the prior art has not addressed the issue of sharps protection for the patients' caregivers and other bystanders. It is therefore an object of this invention to provide a more efficient electrode remover and to reduce the exposure of electrical therapy patients' caregivers to accidental exposure to bloodborne pathogens, microbes, toxins, etc., via an injury caused by unintended contact with a sharp electrode.

It is a further object of this invention to provide a percutaneous electrical therapy system having electrodes and electrode assemblies that are safe, efficacious, inexpensive and easy to use.

Other objects of the invention will be apparent from the description of the preferred embodiments.

SUMMARY OF THE INVENTION

The invention is a percutaneous electrode remover. In a preferred embodiment, the remover includes a housing adapted to be held in a user's hand, the housing having an aperture at a distal end; and an actuator operable by a user to move a percutaneously inserted electrode through the aperture and completely into the housing.

In some embodiments, the remover also includes an electrode engager adapted to engage an exposed portion of an electrode upon operation of the actuator.

In some embodiments of the remover, the actuator is further adapted to be operated by a user's thumb to move the electrode through the aperture.

In some embodiments, the remover also includes a used electrode holder adapted to hold a plurality of electrodes that had been moved into the housing by operation of the actuator.

In some embodiments of the remover, aperture is adapted to cooperate with an alignment element to align the introducer with an electrode insertion site.

The invention is described in more detail below with reference to the drawings.

DETAILED DESCRIPTION OF THE PREFERRED EMBODIMENTS

Percutaneous electrical therapy systems, such as PNT systems, deliver electric current to a region of a patient's tissue through electrodes that pierce the skin covering the tissue. The electric current is generated by a control unit external to the patient and typically has particular waveform characteristics such as frequency, amplitude and pulse width. Depending on the treatment or therapy being delivered, there may be one electrode containing both a cathode and an anode or a plurality of electrodes with at least one serving as a cathode and at least one serving as an anode.

The electrode has a sharp point to facilitate insertion through the patient's skin and to enhance local current density during treatment. Once inserted into the skin, the sharp point may become exposed to pathogens, microbes, toxins, etc. in the patient's tissue and/or blood. After removal of the electrode from the patient's tissue, a caregiver or other bystander may be stuck accidentally with the sharp point of the electrode, thereby exposing the caregiver to any pathogens that may be on the used electrode. This invention therefore provides an electrode remover having a sharp point protection assembly that is efficient and easy to use.

Figure 1:
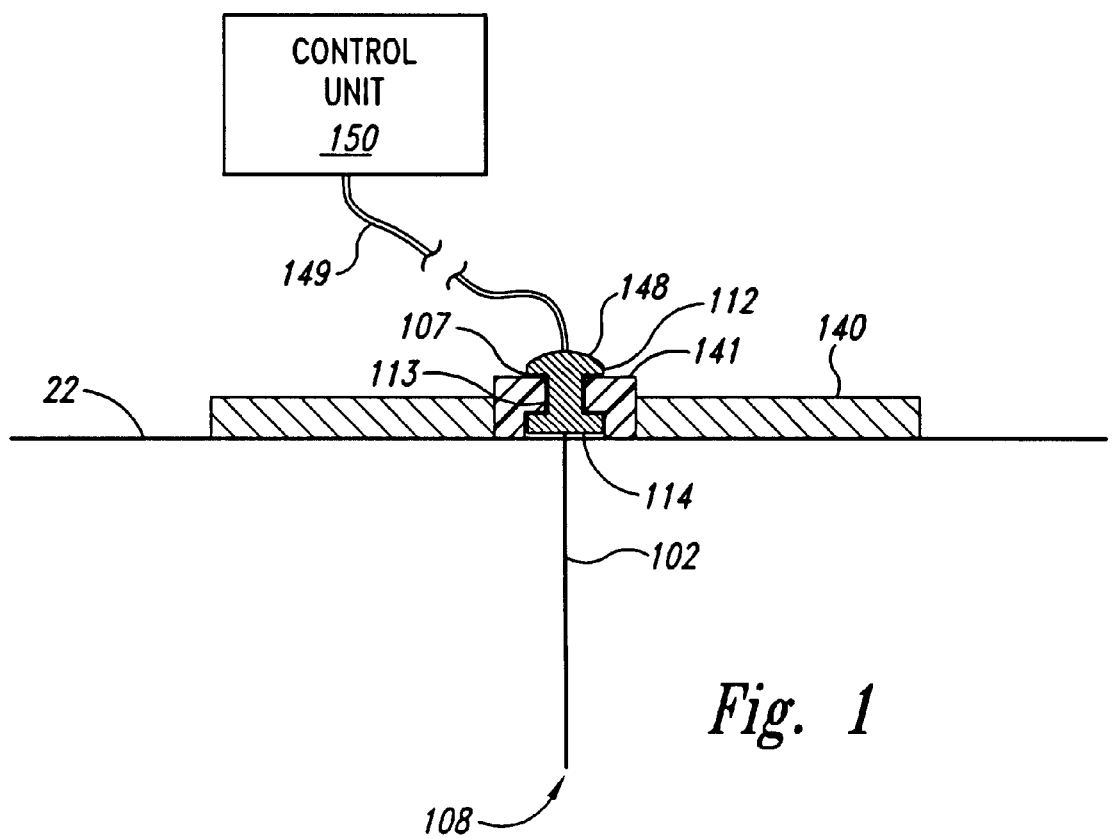
FIG. 1 is a sectional view of a percutaneous electrode in place within a patient's tissue during electrical therapy.

FIG. 1 shows a percutaneous electrode 102 whose sharp point 108 is in place in the tissue beneath a patient's skin 22. During use, electrode 102 is connected to a control unit 150 via a cable 149 attached to an upper wide portion 112 of a handle portion 107 of the electrode. Insertion of the electrode and operation of the control unit and electrode to provide electrical therapy to the patient is explained in more detail in copending patent application [sharps protection], the disclosure of which is incorporated herein by reference.

Electrode 102 is shown deployed through a compressible annular patch 140, which is attached to the patient's skin by adhesive or other suitable means. Patch 140 has a rigid annular member 141 disposed in its center and extending upwardly from it. Rigid member 141 has a smaller diameter opening 142 leading to a larger diameter opening 144. The diameter of opening 142 is slightly smaller than a lower wide portion 114 of a handle portion 107 of electrode 102 and slightly larger than the diameter of a central portion 113 of electrode handle 107. Lower wide portion 114 is preferably made of a resilient and compressible material.

As shown in FIGS. 3–8, remover 200 is designed to work with the electrode and electrode patch assembly of FIG. 1. It should be understood that the remover of this invention can be used with other electrode designs and with or without electrode holding members such as patch 140.

Remover 200 has a housing 202 with an aperture 204 at its distal end. A number of previously undeployed electrodes 102 are stored within housing 202. A pair of rails 214 and 216 hold the electrodes 102 in alignment via the electrode handles 107, as shown. While this embodiment of the remover is designed to provide sharps-safe removal and storage of a plurality of electrodes, the invention applies to removers designed to remove and store one or any number of electrodes.

Figure 2:
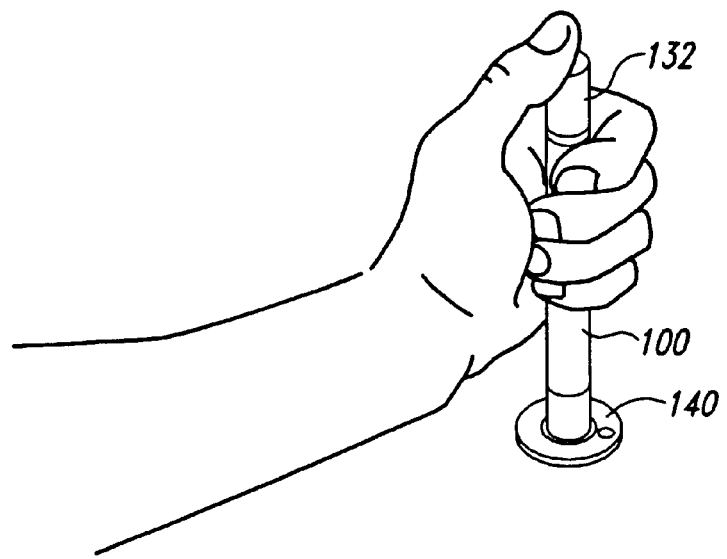
FIG. 2 is an elevational view of an operator using the remover of this invention.
Figure 3:
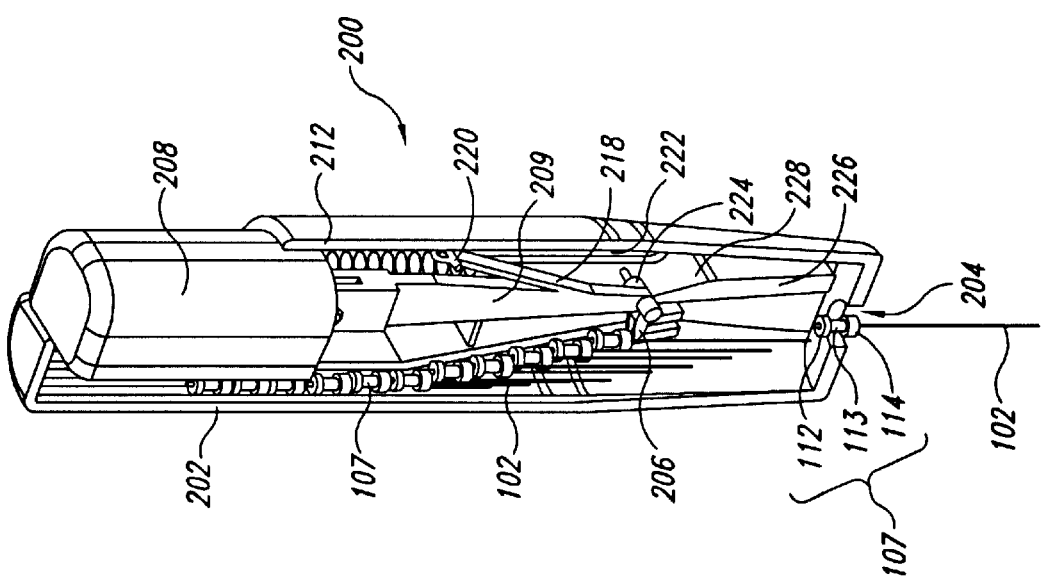
FIG. 3 is a partial sectional view of an electrode remover and sharp point protection assembly according to yet another embodiment of the invention prior to removal of an electrode.

As described above, electrodes for percutaneous electrical therapy are inserted through a patient's skin into underlying tissue with handle portions exposed above the skin. The first step in undeploying and removing an inserted electrode is to line up the exposed handle 107 of an electrode with the remover's aperture 204, as shown in FIGS. 2 and 3, by placing the distal face 205 of remover 200 against the patient's skin or against any portion of the electrode assembly (such as an adhesive patch) surrounding the electrode. While not shown in FIGS. 3–8, aperture 204 is sized to surround an annular member holding an electrode handle of an electrode assembly, such as that shown in FIG. 1, the sharp point of which has been inserted through a patient's skin.

An electrode engagement fork 206 is pivotably attached to a longitudinally movable actuator 208 via an arm 209 and a hinged pivot 210. A coil spring 212 biases actuator 208 upwards towards the actuator and fork position shown in FIG. 8. A leaf spring 218 extends from arm 209. A cross-bar 220 at the end of leaf spring 218 slides in groove 222 and a corresponding groove (not shown) on the other side of housing 202. Leaf spring 218 is in its relaxed state in the position shown in FIG. 3. In this position, a cross-bar 224 extending from the distal end of arm 209 adjacent fork 206 lies at the top of a camming member 226 and a corresponding camming member (not shown) on the other side of housing 202.

Figure 4:
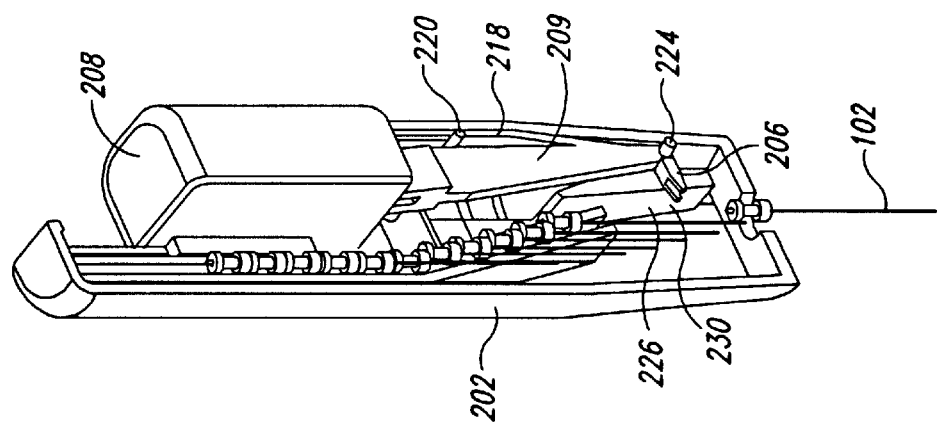
FIG. 4 is a partial sectional view of the electrode remover and sharp point protection assembly of FIG. 3 partially actuated but prior to removal of an electrode.

Downward movement of actuator 208 (in response, e.g., to pressure from a user's thumb) against the upward force of spring 212 moves cross-bar 224 against a first camming surface 228 of camming member 226, as shown in FIG. 4. Camming surface 228 pushes cross-bar 224 of arm 209 against the action of leaf spring 218 as actuator 208, arm 209 and fork 206 move downward.

Figure 5:
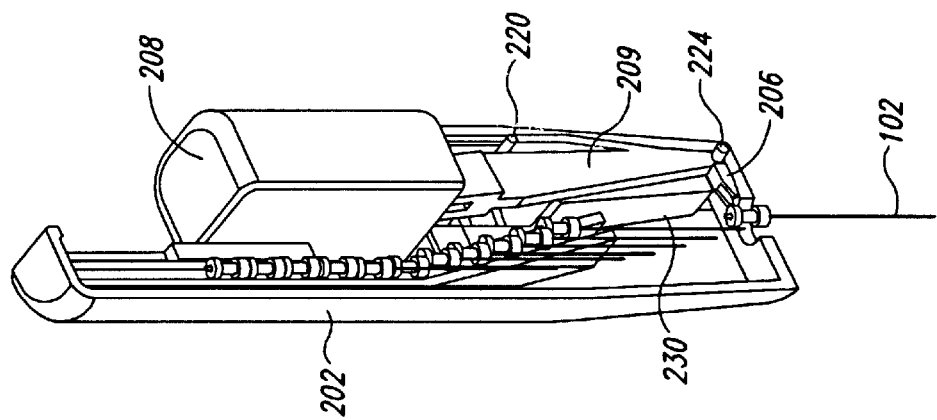
FIG. 5 is a partial sectional view of the electrode remover and sharp point protection assembly of FIG. 3 partially actuated but prior to removal of an electrode.
Figure 6:
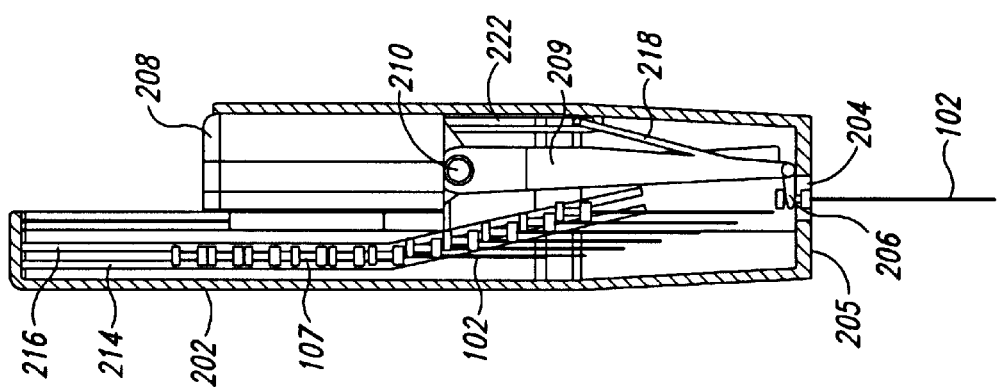
FIG. 6 is a partial sectional view of the electrode remover and sharp point protection assembly of FIG. 3 partially actuated and engaged with an electrode but prior to removal of the electrode.

FIG. 5 shows the limit of the downward movement of fork 206. At this point, cross-bar 224 clears the camming member 226, and leaf spring 218 rotates fork 206 and arm 209 about pivot 210 to engage fork 206 with electrode handle 107, as shown in FIG. 6. The tine spacing of fork 206 is shorter than the diameter of the upper wide portion 112 of electrode handle 107 but wider than the diameter of the narrow middle portion 113 of electrode handle 107.

Figure 7:
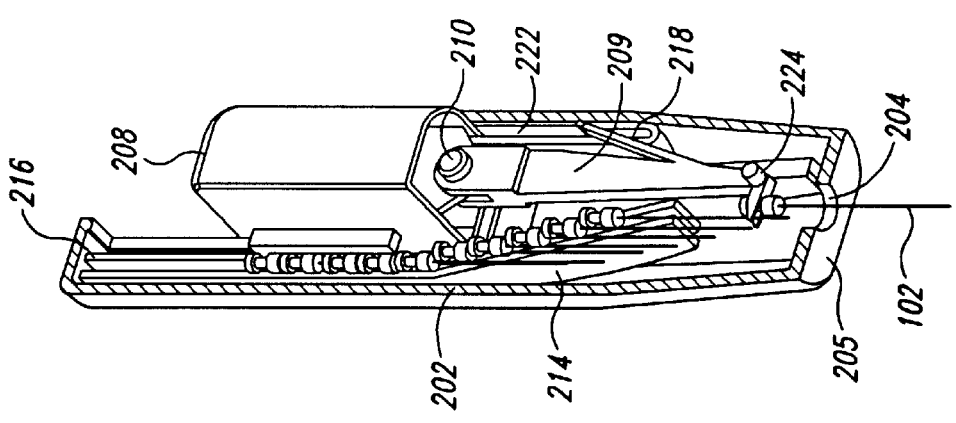
FIG. 7 is a partial sectional view of the electrode remover and sharp point protection assembly of FIG. 3 during removal of an electrode.

Release of actuator 208 by the user permits spring 212 to move actuator 208, arm 209 and fork 206 proximally. The engagement between fork 206 and electrode handle 107 causes the electrode to begin to move proximally with the fork out of the patient and into the remover housing, as shown in FIG. 7. At this point, cross-bar 224 is now engaged with a second camming surface 230 of camming member 226. Camming surface 230 pushes cross-bar 224 against the action of leaf spring 218 in the other direction (to the left in the view shown in FIG. 7) as the electrode, fork and arm rise under the action of coil spring 212.

Figure 8:
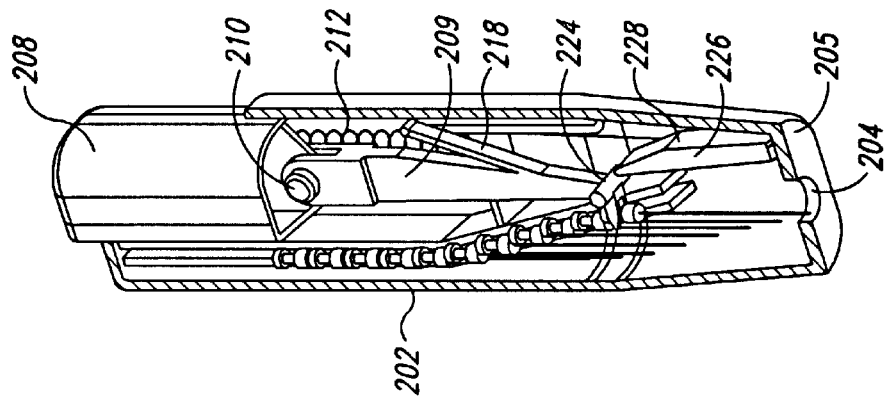
FIG. 8 is a partial sectional view of the electrode remover and sharp point protection assembly of FIG. 3 after removal of an electrode.

The electrode and fork continue to rise until they reach the upward limit of their permitted motion, as shown in FIG. 8. At this point, electrode handle 107 has engaged rails 214 and 216 and the most recent electrode previously stored in remover 200. Electrode handle 107 pushes against the electrode handle of the previously stored electrode handle, which in turn pushes against any electrode handles stored above it in the stack. In this manner, the latest electrode removed by remover 200 goes into the bottom of the stack of used electrodes stored in remover 200. Now that the sharp point 108 of electrode 102 is safely inside housing 202, remover 200 can be withdrawn from the site on the patient's skin through which the electrode had been inserted. Once cross-bar 224 clears the top of camming member 226, and leaf spring 218 moves arm 209 back to the center position shown in FIG. 3.

It should be noted that remover 200 provides sharp point protection for the entire electrode undeployment and removal process. Once all electrodes have been removed, the used electrodes can be safely transported in the sharps-safe container provided by the housing 202 of remover 200.

Modifications of the above embodiments of the invention will be apparent to those skilled in the art. For example, while the invention was described in the context of percutaneous electrical therapy in which electrodes are used to deliver electricity to a patient, the features of this remover may be used to remove electrodes designed for medical monitoring and/or diagnosis. In addition, the remover features of this invention may be used with acupuncture needles or other needles not used for conducting electricity to or from a patient.

What is claimed is:

1. A percutaneous electrode remover comprising:
   a housing configured to be held in a user's hand, the housing having an aperture at a distal end;
   an actuator operable by a user to move a percutaneously inserted electrode through the aperture and completely into the housing; and
   a used electrode holder configured to hold a plurality of electrodes that have been moved into the housing by operation of the actuator.

2. The remover of claim 1 further comprising an electrode engager configured to engage an exposed portion of an electrode upon operation of the actuator.

3. The remover of claim 1 wherein the actuator is further configured to be operated by a user's thumb to move the electrode through the aperture.

4. The remover of claim 1 wherein the aperture is configured to cooperate with an alignment element to align an introducer with an electrode insertion site.

* * * * *